United States Patent
Kleiner et al.

(10) Patent No.: US 6,184,405 B1
(45) Date of Patent: Feb. 6, 2001

(54) PROCESS FOR PREPARING ALUMINUM SALTS OF ORGANIC PHOSPHORIC ACIDS

(75) Inventors: Hans-Jerg Kleiner, Kronberg; Thomas Seitz, Heddesheim, both of (DE)

(73) Assignee: Ticona GmbH (DE)

( * ) Notice: Under 35 U.S.C. 154(b), the term of this patent shall be extended for 0 days.

(21) Appl. No.: 09/297,548

(22) PCT Filed: Oct. 23, 1997

(86) PCT No.: PCT/EP97/05855

§ 371 Date: May 3, 1999

§ 102(e) Date: May 3, 1999

(87) PCT Pub. No.: WO98/20012

PCT Pub. Date: May 14, 1998

(30) Foreign Application Priority Data

Nov. 4, 1996 (DE) .............................. 196 45 125

(51) Int. Cl.$^7$ .......................... C07F 9/6568; C07F 9/48; C07F 9/30; C07F 9/09
(52) U.S. Cl. ........................................................ 556/174
(58) Field of Search ........................... 556/174; 558/133; 562/8

(56) References Cited

U.S. PATENT DOCUMENTS

| | | | | |
|---|---|---|---|---|
| 3,494,949 | * | 2/1970 | Monroe et al. ...................... | 556/174 |
| 4,481,026 | * | 11/1984 | Prisbylla ........................... | 556/174 X |
| 5,174,991 | * | 12/1992 | Omatsu et al. ................... | 556/174 X |
| 5,773,556 | * | 6/1998 | Kleiner et al. ..................... | 528/321 |
| 5,891,226 | * | 4/1999 | Kleiner et al. ..................... | 562/8 X |

FOREIGN PATENT DOCUMENTS

700042 * 6/1967 (BE) .
0 699 708 A2 * 3/1996 (EP) .

OTHER PUBLICATIONS

Derwent World Patents Index, ©Derwent Information Ltd., Accession No. 1968–98748P (1968).*

* cited by examiner

Primary Examiner—Michael G. Ambrose
(74) Attorney, Agent, or Firm—Connolly Bove Lodge & Hutz LLP

(57) ABSTRACT

The invention concerns a process for preparing salts of organic acids of phosphorus. The organic acid is reacted with aluminum hydroxide in the presence of a polar solvent selected from acetic acid, propionic acid, methanol, ethanol, n-propanol, isopropanol, butanol, acetone, methyl ethyl ketone, tetrahydrofuran, dioxane, and acetonitrile.

4 Claims, No Drawings

PROCESS FOR PREPARING ALUMINUM SALTS OF ORGANIC PHOSPHORIC ACIDS

The invention relates to a process for the preparation of aluminum salts of organic acids of phosphorus. More specifically, these are phosphonic half-esters, phosphinic acids and phosphonous acids.

The aluminum salts of these organic phosphoric acids are valuable flame retardants.

Aluminum salts of phosphonic half-esters have hitherto been prepared by reacting aluminum chloride with phosphonic diesters (EP-A 245 207), by reacting elemental aluminum with phosphonic diesters (EP-A 299 922) and by reacting aluminum hydroxide with phosphonic diesters in the absence of water at 180° C. (EP-A 327 496). Aluminum salts of phosphinic acids and cyclic phosphinic acids (1-hydroxy-dihydrophosphole oxides and 1-hydroxy-phospholane oxides) have hitherto been prepared by reaction with aluminum hydroxide in water (EP-A2-0 699 708).

The reaction of phosphonic diesters with aluminum chloride, aluminum or aluminum hydroxide inevitably leads to undesired byproducts such as alkyl chlorides, alcohols, carbon monoxide, ethylene, ethane and low dialkyl ethers. The phosphonic diesters also have to be used in excess. The reaction of organic phosphoric acids in water with aluminum hydroxide is in itself technically simple. A disadvantage is the long reaction time which is required.

There was therefore a need to develop a process which avoids the aforementioned disadvantages, is industrially feasible without great expenditure and, moreover, makes the desired products available both in high yield and in high purity.

Surprisingly, this object was achieved by a process for the preparation of aluminum salts of organic phosphoric acids of the formula (I)

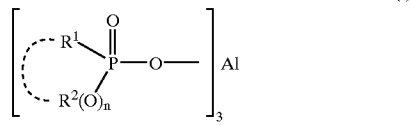

(I)

where $R^1$ is a saturated or unsaturated or unbranched $C_1–C_8$, preferably $C_1–C_4$ alkyl, or phenyl, when n=0

$R^2$ is as defined for $R^1$ or is hydrogen, it also being possible for $R^1$ and $R^2$ to be joined to give a saturated or unsaturated ring, when n=1

$R^2$ is a saturated $C_1–C_4$ preferably $C_1$, alkyl, which comprises reacting, in the absence or presence of water, organic phosphoric acids of the formula (II)

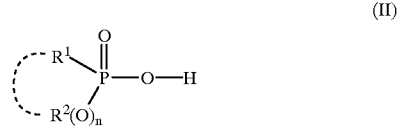

(II)

where $R^1$, $R^2$ and n are as defined above, with aluminum hydroxide in the presence of polar solvents.

Surprisingly, it was found that the chemically largely inert aluminum hydroxide reacts more quickly in the presence of polar solvents.

Examples of organic phosphoric acids which may be mentioned are:
1. Phosphonic monoesters: monomethyl methanephosphonates, monomethyl propanephosphonates, monoethyl ethanephosphonates, mono-n-propyl phenylphosphonates.
2. Phosphinic acids: dimethylphosphinic acid, ethylmethylphosphinic acid, propylmethylphosphinic acid, methylphenylphosphinic acid.
3. Cyclic phosphinic acids: 1-hydroxy-3-methyl-2,5-dihydro-1H-phosphole 1-oxide, 1-hydroxy-2,3-dihydro-1H-phosphole 1-oxide, 1-hydroxy-2,5-dihydro-1H-phosphole 1-oxide, 1-hydroxy-1H-phospholane 1-oxide and 1-hydroxy-3-methyl-1H-phospholane 1-oxide.
4. Phosphonous acids: methanephosphonous acid, propanephosphonous acid, octanephosphonous acid, phenylphosphonous acid.

Polar solvents which may be mentioned in particular are: acetic acid, propionic acid, methanol, ethanol, propanol, butanol, acetone, methyl ethyl ketone, tetrahydrofuran, dioxane and acetonitrile. Acetic acid and isopropanol are particularly preferred.

The solvents can also be used as mixtures. In particular, mixtures with water can be used advantageously.

The reaction temperatures are 50 to 200° C., preferably 70 to 100° C. The reaction is preferably carried out under reflux conditions. At higher temperatures, the reaction may be carried out under pressure.

The reaction components can be mixed with the solvents and are then usually stirred for several hours at the desired reaction temperature. It can also be advantageous to introduce the solvent or solvent mixture with aluminum hydroxide, and slowly meter in the organic phosphoric acid at the reaction temperature with continuous stirring. After the reaction has finished, the mixture is filtered off with suction and the aluminum salt produced is dried. In the process of the present invention, the aluminum salts which are produced are finely particulate with a mean particle size of from 2 to 25 μm. It is not therefore necessary to grind these salts after drying for plastics compounding.

EXAMPLE 1

Aluminum Salt of Monomethyl Methanephosphonate 99 g (0.9 mol) of monomethyl methanephosphonate, 23.4 g (0.3 mol) of aluminum hydroxide and 330 ml of water/solvent mixture are stirred at the reaction temperature for the reaction period. Filtration with suction is then carried out, followed by washing with water/solvent mixture and drying at 140–150° C. in a vacuum drying cabinet to give the reaction product.

| No. | Water/solvent mixture | Reaction temperature [° C.] | Reaction period [h] | Yield [g] | % of theory |
|---|---|---|---|---|---|
| a | Water/isopropanol 1:1 | 75 | 24 | 96.7 | 91 |
| b | Water/isopropanol 1:1 | 75 | 12 | 97.5 | 92 |
| c | Water/acetic acid 1:1 | 80–90 | 24 | 92.9 | 87.5 |

EXAMPLE 2

Aluminum Salt of Ethylmethylphosphinic Acid with Acetic Acid or Propionic Acid as Solvent 54 g (0.5 mol) of ethylmethylphosphinic acid, 13 g (0.167 mol) of aluminum hydroxide and 154 ml of solvent or solvent mixture are stirred at the reaction temperature for the reaction period. Cooling and filtration with suction are then carried out, followed by drying at 140–150° C. in a vacuum drying cabinet to give the reaction product.

| No. | Water/solvent mixture | Reaction temperature [° C.] | Reaction period [h] | Yield [g] | % of theory |
|---|---|---|---|---|---|
| a | Acetic acid | 105 | 4.5 | 54 | 93 |
| b | Acetic acid/water 2:1 | 86 | 5 | 50.1 | 86 |
| c | Propionic acid | 115–120 | 5 | 52.2 | 90 |

EXAMPLE 3

Aluminum Salt of Ethylmethylphosphinic Acid with Other Polar Solvents 108 g (1.0 mol) of ethylmethylphosphinic acid, 26 g (0.333 mol) of aluminum hydroxide and 324 ml of solvent or solvent mixture are stirred at the reaction temperature for the reaction period. Cooling, filtration with suction and drying are then carried out.

| No. | Water/solvent mixture | Reaction temperature [° C.] | Reaction period [h] | Yield [g] | % of theory |
|---|---|---|---|---|---|
| a | Isopropanol | 85 | 24 | 92.5 | 80 |
| b | Isopropanol/water 1:1 | 85 | 7.5 | 110.9 | 96 |
| c | Methanol/water | 80 | 24 | 100.8 | 88 |

EXAMPLE 4

Aluminum Salt of Ethylmethylphosphinic Acid 130 g (1.67 mol) of aluminum hydroxide and 1620 ml of acetic acid are heated to reflux with stirring, and 540 g (5.0 mol) of ethylmethylphosphinic acid are added dropwise over the course of 3.5 hours. The mixture is then maintained under reflux for about another 4 hours. Filtration with suction is carried out, followed by drying in a vacuum drying cabinet at 140° C., giving 573 g. This corresponds to a yield of 98.6% of theory.

EXAMPLE 5

Aluminum Salt of Methylpropylphosphinic Acid 91.5 g (0.75 mol) of methylpropylphosphinic acid are dissolved in 240 ml of acetic acid, and 19.5 g (0.25 mol) of aluminum hydroxide are added. The mixture is then heated at 110° C. with stirring for 5 hours, cooled and filtered with suction. Drying in a vacuum drying cabinet at 140° C. gives 85 g. This corresponds to a yield of 87% of theory.

EXAMPLE 6

Aluminum Salt of 1-hydroxy-1H-phospholane 1-oxide 10 g (0.083 mol) of 1-hydroxy-1H-phospholane 1-oxide and 2.2 g (0.028 mol) of aluminum hydroxide are stirred into 28 ml of acetic acid at 105° C. for 1.5 hours. The mixture is then filtered with suction, giving 10.5 g which after drying do not melt up to 360° C. This corresponds to a yield of 98% of theory.

EXAMPLE 7

Aluminum Salt of 1-hydroxy-3-methyl-1H-phospholane 1-oxide 26.8 g (0.200 mol) of 1-hydroxy-3-methyl-1 H-pholane 1-oxide and 5.2 g (0.067 mol) of aluminum hydroxide are stirred into 33 g of acetic acid at 105° C. for 4 hours. The mixture is then filtered with suction, giving 26.2 g which after drying do not melt up to 360° C. This corresponds to a yield of 92% of theory.

EXAMPLE 8

Aluminum Salt of 1-hydroxy-2,5-dihydro-1H-phosphole 1-oxide 10 g (0.085 mol) of 1-hydroxy-2,5-dihydro-1H-phosphole 1-oxide and 2.2 g (0.028 mol) of aluminum hydroxide are stirred into 28 ml of acetic acid at 105° C. for 1.5 hours. The mixture is then filtered with suction, giving 10.5 g which after drying do not melt up to 360° C. This corresponds to a yield of 97% of theory.

EXAMPLE 9

Aluminum Salt of Methanephosphonous Acid 80 g (1.0 mol) of methanephosphonous acid are dissolved in 110 ml of acetic acid, and 26 g (0.33 mol) of aluminum hydroxide are added with stirring. The mixture is then heated at 110° C. for 5 hours. Cooling, filtration with suction and drying at 140° C. in a vacuum drying cabinet give 82.7 g, which corresponds to a yield of 94% of theory.

What is claimed is:

1. A process for the preparation of an aluminum salt of an organic acid of phosphorus, which comprises reacting the organic acid of phosphorus with a aluminum hydroxide in a polar solvent, and wherein the organic acid of phosphorus is selected from the group consisting of phosphonic monoester, phosphinic acid, cyclic phosphinic acid and phosphonous acid and wherein the polar solvent is selected from the group consisting of acetic acid, propionic acid, methanol, ethanol, n-propanol, isopropanol, butanol, acetone, methyl ethyl ketone, tetrahydrofuran, dioxane and acetonitrile.

2. The process of claim 1, wherein the organic acid of phosphorus is reacted with aluminum hydroxide in the presence of water.

3. The process of claim 1, wherein the process is carried out at a reaction temperature in the range from 50° C. to 200° C.

4. The process of claim 1, wherein a salt of an organic acid of phosphorus with a mean particle size of from 2 to 25 µm is formed in the process.

* * * * *

UNITED STATES PATENT AND TRADEMARK OFFICE
CERTIFICATE OF CORRECTION

PATENT NO. : 6,184,405
DATED : February 6, 2001
INVENTOR(S) : Hans-Jerg Kleiner and Thomas Seitz It is certified that error appears in the above-identified patent and that said Letters Patent is hereby corrected as shown below:

In the claims, column 4, line 41 (claim 1, line 3), before the word "aluminum"

delete —a—.

Signed and Sealed this

Fifth Day of June, 2001

Attest:

Attesting Officer

NICHOLAS P. GODICI
Acting Director of the United States Patent and Trademark Office